United States Patent [19]

Stache et al.

[11] Patent Number: 5,824,670
[45] Date of Patent: Oct. 20, 1998

[54] 17-DEOXYCORTICOSTEROID-21-[O] CARBOXYLIC ESTERS, PROCESSES FOR THEIR PREPARATION AND PHARMACEUTICALS CONTAINING THESE COMPOUNDS

[75] Inventors: Ulrich Stache, Hofheim; Hans-Georg Alpermann, Königstein; Manfred Bohn, Hofheim, all of Germany

[73] Assignee: Hoechst Aktiengesellschaft, Frankfurt am Main, Germany

[21] Appl. No.: 529,668

[22] Filed: Sep. 18, 1995

[30] Foreign Application Priority Data

Sep. 20, 1994 [DE] Germany ............... 44 33 374.9

[51] Int. Cl.$^6$ ............... A61K 31/57; C07J 5/00; C07J 43/00
[52] U.S. Cl. ............... 514/177; 514/178; 514/179; 514/180; 514/181; 552/588; 552/601; 552/602; 540/2; 540/113; 540/114
[58] Field of Search ............... 552/588, 601, 552/602; 514/177, 178, 179, 180, 181; 540/2, 113, 114

[56] References Cited

U.S. PATENT DOCUMENTS

| | | | |
|---|---|---|---|
| 2,755,292 | 7/1956 | Hewett | 260/397.4 |
| 2,783,226 | 2/1957 | Gould et al. | 260/239.55 |
| 4,086,254 | 4/1978 | Wierenga | 260/397.45 |
| 4,377,575 | 3/1983 | Stache et al. | |

FOREIGN PATENT DOCUMENTS

| | | | |
|---|---|---|---|
| 0127829 | 12/1984 | European Pat. Off. | |
| 2381065 | 9/1978 | France | C07J 5/00 |
| 1131668 | 7/1962 | Germany | |
| 2047105 | 3/1972 | Germany | C07C 169/34 |
| 2709078 | 9/1977 | Germany | C07J 5/00 |
| 2617655 | 11/1977 | Germany | C08J 5/00 |
| 2920726 | 11/1980 | Germany | C07J 5/00 |
| 131448 | 12/1965 | New Zealand | |
| 142273 | 5/1969 | New Zealand | |
| 153451 | 4/1971 | New Zealand | |
| 157357 | 11/1971 | New Zealand | |
| 165601 | 10/1972 | New Zealand | |
| 179952 | 4/1978 | New Zealand | |
| 185296 | 4/1980 | New Zealand | |
| 187431 | 5/1980 | New Zealand | |
| 199600 | 9/1984 | New Zealand | |
| 229694 | 3/1992 | New Zealand | |
| 229696 | 3/1992 | New Zealand | |
| 237559 | 4/1993 | New Zealand | |
| 495969 | 10/1970 | Switzerland | |

OTHER PUBLICATIONS

M. Wall, et al.; The Effects of Some Steroidal Alkylating Agents on Experimental Animal Mammary Tumor and Leukemia Systems; Sep. 1969; vol. 12, No. 5, pp. 810–818.

Courrier, et al.; "Endocrinologie.—Sur les propriétés biologiques des allénolates de désoxycorticostérone."; Comptes Rendus des Séances de L'Académie des Sciences; Jul. 5, 1954; vol. 239, pp. 14–16.

A. Ercoli, et al.; "Steroids with side chain containing a ketol group"; Chemical Abstracts; Jul. 10, 1957; vol. 51, No. 13, col. 9723, Abstract.

Hiroyuki, et al.; "Synthesis and reactivity of anthracene–a–carbonylazide as a fluorescent derivatization reagent for alcohols"; Chemical Abstracts, vol. 112, 1990, p. 696, Abstract No. 112: 178253d.

*Primary Examiner*—José G. Dees
*Assistant Examiner*—Barbara Badio
*Attorney, Agent, or Firm*—Finnegan, Henderson, Farabow, Garrett & Dunner, L.L.P.

[57] ABSTRACT

17-Deoxycorticoid-21-carboxylic esters of the formula I

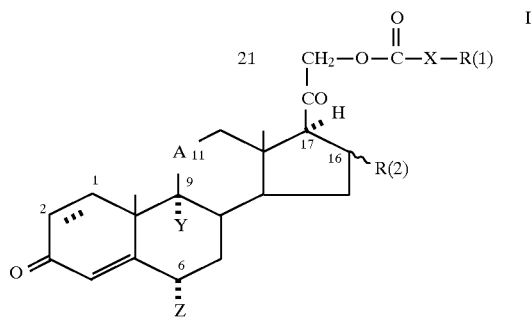

are described, in which A is CHOH and CHCl, CH$_2$, C=O or 9(11) double bond; Y is H, F or Cl; Z is H, F or CH$_3$; R(1) is aryl or hetaryl and R(2) is H or methyl. They are obtained by reacting a compound of the formula II,

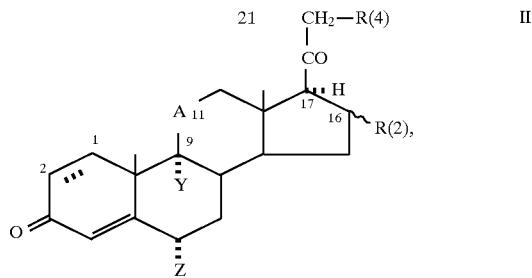

in which R(4) is OH, with an activated carboxylic acid of the formula III,

R(5)-CO—X-R(1)                                III.

The compounds I possess very strong local and topical antiinflammatory activity and exhibit a very good ratio of local to systemic antiinflammatory effect, which ratio is often clearly superior to that of structurally related corticoid 21-esters which do not carry any aryl or hetaryl group in the 21-ester residue or to that of analogous 17-deoxycorticoids having an unesterified, that is a free, 21-hydroxyl group.

11 Claims, No Drawings

17-DEOXYCORTICOSTEROID-21-[O] CARBOXYLIC ESTERS, PROCESSES FOR THEIR PREPARATION AND PHARMACEUTICALS CONTAINING THESE COMPOUNDS

The invention relates to 17-deoxycorticoid-21-carboxylic esters of the formula I

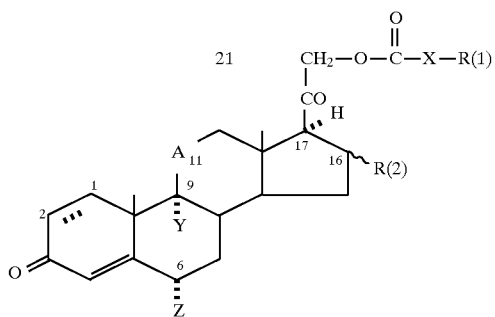

in which:
- A is CHOH and CHCl in arbitrary steric arrangement, $CH_2$, C=O or 9(11) double bond,
- Y is hydrogen, fluorine or chlorine,
- Z is hydrogen, fluorine or methyl,
- R(1) is optionally substituted or fused aryl or hetaryl,
- X is ($C_1$–$C_4$)-aliphatic hydrocarbon; saturated, also unsaturated once from $C_2$, also unsaturated more than once from $C_3$, or cyclic branched by alkyl groups, R(5)-CO—X—R(1) inserted or substituted by heteroatoms O, S or N; the 1,2 positions are saturated or unsaturated (1,2 double bond);
- R(2) is hydrogen, α-methyl or β-methyl.

17-Deoxycorticoid-21-carboxylic esters of the formula I are preferred in which:
- R(1) is defined as above;
- A is CHOH (in the β configuration);
- Y is F;
- Z is hydrogen;
- R(2) is α-methyl.

The invention also relates to a process for preparing a compound I, wherein
a) a compound of the formula II

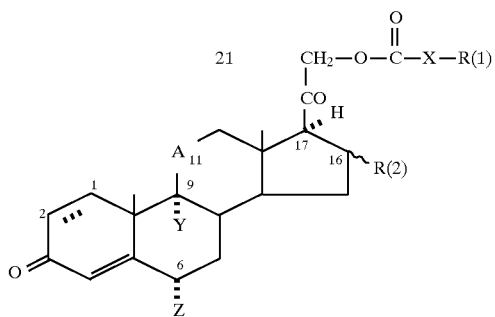

in which R(4) is OH and the remaining substituents have the abovementioned meanings, a1) is reacted with an activated carboxylic acid of the formula III, preferably a halide and anhydride or azolide,

R(5)-CO—X—R(1)                III in which
X and R(1) have the abovementioned meanings, and
R(5) is Cl, Br, —O[—CO—X—R(1)], —O—C(O)CF, or another activated acid radical, or a2) is reacted with a carboxylic acid of the formula III itself, in which
R(6) is OH
and the other substituents are given in formula III, in the presence of water-eliminating reagents (DCCI, etc.), or wherein b) compounds of the formula II

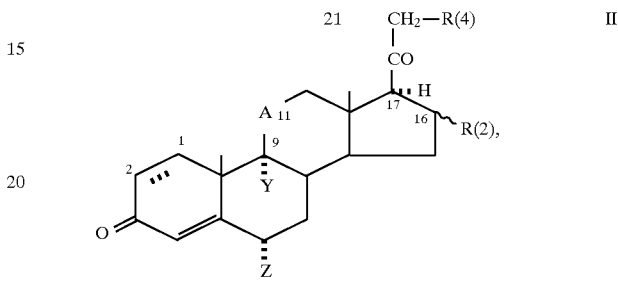

in which R(4) is Br, I, or a sulfonic aryl ester group or sulfonic alkyl ester group, and the other substituents have the meaning given in formula I, are reacted with a salt, preferably a K or Na salt or a trialkylammonium salt, of a carboxylic acid of the formula III,

R(5)-CO—X—R(1)                III in which
R(5) is —[O—$Me^+$], and
and the other substituents have the meanings given in formula III,
$Me^+$ preferably being the cation of an alkali metal salt or of a trialkylammonium salt.

The stippled line between carbon atoms 1 and 2 indicates that this bond can be a single bond or an unsaturated bond.

The aryl and hetaryl groups which are preferred are: phenyl, naphthyl, biphenylyl, phenyloxy, phenylthio, benzoyl, thienyl, furyl, thiazolyl, pyrrolyl, imidazolyl, pyridyl, indolyl, xanthonoxy and flavonyl. These aryl and heteraryl groups are either unsubstituted or substituted by 1–3 substituents selected from the group consisting of ($C_1$–$C_{12}$)-alkyl (saturated or unsaturated), F, Cl, Br, I, ($C_1$–$C_8$)-alkoxy (saturated or unsaturated; two adjacent groups can also form methylenedioxy groups), $NO_2$, ($C_1$–$C_4$)-alkylthio, phenoxy, benzoyl, NR(6)R(7) with R(6) and R(7) being identical or different and being hydrogen, ($C_1$–$C_4$)-alkyl, ($C_1$–$C_4$)-acyl, t-butyloxycarbonyl or ($CH_2$)—$CH_2Cl$; in addition, the aromatic rings in the substituents on the aryl and heteraryl groups can, for their part, be unsubstituted or be substituted by 1–3 substituents selected from the group consisting of ($C_1$–$C_4$)-alkyl, ($C_1$–$C_4$)-alkoxy, F, Cl, Br and I. As a rule, the 17-deoxy steroids having a free 21-hydroxyl group of the formula II [R(4)=OH] which are required as starting compounds are known from the literature.

The 17-deoxy steroids in which R(4) is Br, I, —$OSO_2$-aryl or —$OSO_2$-alkyl in formula II are prepared in analogy with the U.S. Pat. No. 4,377,575 (HOE 78/F 082). The following 17-deoxy corticosteroids are examples of those which are suitable in this context:
corticosterone (11β,21-dihydroxypregn-4-on-3,20-dione)
deoxycorticosterone (11-deoxycorticosterone)

16α-methyl-1(2)-dehydrocorticosterone
6α-fluoro-16α-methyl-1(2)-dehydrocorticosterone (=fluocortolone)
9α-fluoro-16α-methyl-1(2)-dehydrocorticosterone (=deoxymethasone)
diflucortolone
clocortolone
16α-methyl-1(2),9(11)-di-dehydrocorticosterone
6α, 9α-difluorocorticosterone
9α-fluorocorticosterone
6α-methylcorticosterone
6α-fluorocorticosterone
11α-hydroxy-1(2)-dehydro-11-deoxycorticosterone
6α,16α-dimethylcorticosterone
11-dehydrodeoxymethasone The carboxylic acids of the formula III R(5) is OH which are used as reaction partners, and their activated derivatives, such as the halides R(5)=Cl, Br or I, or their anhydrides, or their azolides R(5) is imidazolide or triazolide, or their salts [R(5) is (Me$^+$O$^-$)—, preferably (K$^+$O$^-$)— or (Na$^+$O$^-$)—], are as a rule known and are prepared, where appropriate, by general preparative methods. Examples of carboxylic acids according to formula III R(5) is OH which can be used in accordance with the invention are to be found in the list at the end of the text prior to the claims.

All carboxylic acids coming into this category carry, in their acid radical, an aryl or hetaryl group which is optionally substituted by halogen, alkyl, alkoxyl, acyl, thioalkyl, thioacyl, nitro, amino, aminoalkyl, amido, cyano, oxyacyl, oxyaryl, etc., or is optionally fused. The aryl and hetaryl groups are essential constituents of the invention.

As is demonstrated in the pharmacological section, 17-deoxycorticoid-21-carboxylic esters of this type (=21-aryl ester or 21-hetaryl ester type), in particular, often exhibit qualities of effect which are clearly superior, as regards the local/systemic ratio of antiinflammatory effect, to those of structurally related corticoid 21-carboxylic esters which do not carry any aryl or hetaryl group in the 21-acid residue and/or to those of 17-deoxycorticoids having an unesterified free 21-hydroxy group.

Detailed description of the conduct of the individual reactions in the processes for preparing the products according to Formula I according to the invention:
Regarding process variant a In order to prepare 21-carboxylic esters of the abovementioned type, either carbonyl halides or carboxylic azolides of the formula IV

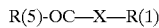

in which:
R(5) is Cl, Br, I, or

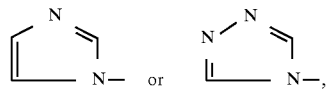

R(1) and X have the meanings given for formula III, or carboxylic anhydrides of the formula V

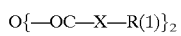

in which:
R(1) and X have the meanings given for formula III, are preferably used. In both cases, the carboxylic acids on which they are based, and which are given in the list,
can be used, preferably their carbonyl chlorides, carboxylic anhydrides, carboxylic imidazolides and carboxylic triazolides.

R(5) in formula IV can also comprise other groups which activate the carboxyl group in carboxylic acids for esterification, such as, for example, —O—CO—CF$_3$, or the activated carboxylic acids which can be prepared from phosphonic or phosphinic anhydrides (e.g. propylphosphonic anhydride) or polyphosphoric anhydride (PPA).

Additional phosphorus reagents which can bring about mild esterification of organic carboxylic acids with the 21-alcohol group of corticoid 17-alkyl carbonates are cited or described in the literature references Synth. Commun. 13, 471 ff (1983) and Synth. Commun. 14, 515 ff (1984).

In order to carry out the esterification using a carbonyl halide or carboxylic anhydride, the steroid component is dissolved in an inert solvent, for example in an ether, such as dioxane, tetrahydrofuran or diglyme, or in optionally halogenated hydrocarbons, such as benzene, toluene, cyclohexane, methylene chloride or chloroform, or in acetone, or in a mixture of these solvents. In order to remove the hydrohalic acid which is produced in the reaction, 1 to 1000 molar equivalents of a tertiary base, such as pyridine, quinoline, triethylamine, dimethylaniline, dimethylaminopyridine, etc., are added. However, an inorganic base, such as sodium hydrogen carbonate or calcium carbonate, can also be used for removing the acid. 1 to 200 molar equivalents, preferably 1–3 molar equivalents, of one of the above-listed acylating agents, optionally dissolved in one of the above-listed solvents, are then added dropwise at a temperature of −40° C. up to the boiling point of the solvent used, preferably at a temperature of 0° C. to 25° C. Subsequently, the reaction mixture is left to stand for one to 120 hours at a temperature of −40° C. up to the boiling point of the solvent, preferably at a temperature of 0° C. to 25° C.

When using carboxylic anhydrides as acylating agents, it is now and then advantageous not to add solvents. As a rule, it is sufficient simply to add the organic base, preferably pyridine, to the acid anhydride, which may optionally be used in excess.

Particularly in the case of sensitive (and sometimes unstable) carboxylic acid derivatives of the abovementioned type, in particular when using phenylacetyl chlorides or anhydrides and hetarylacetyl chlorides and anhydrides, it is of great preparative advantage, and of great advantage with regard to the selectivity of the reaction, if the 17-deoxycorticoids having a free 21-hydroxyl group are reacted with 1 to 4 molar equivalents of the chloride or anhydride at −10° to +6° (maximum 20° C.) in chlorinated hydrocarbons, such as, preferably, dichloromethane, and with 1 to 4 molar equivalents of a pyridine base, preferably dimethylaminopyridine.

Under these circumstances, the reaction products of the formula I are obtained in high purity, with negligible quantities of byproducts, in particular 11-acylated products (monitoring of the course of the reactions with TLC), that is the reactions are highly regioselective with regard to conversion of the 21-hydroxyl group.

In the case of the reactions with carbonyl chlorides, absolute dioxane or tetrahydrofuran is frequently advantageously added to the reaction mixture, e.g. in the case of benzoyl chloride, where the ratio of dioxane/pyridine is approximately 1:1; in addition, in order to accelerate the reaction, the reaction mixture is often, particularly in the case of sterically hindered or less reactive carbonyl chlorides or carboxylic anhydrides, heated to about 60° C. (monitoring of the course of the reaction with TLC).

The reaction products can be characterized using thin layer chromatography (TLC); in this context, the reaction products have RF values of about 0.6 to 0.8. As a rule, the reaction products are characterized by mass spectra using MS=m/z= ... (M+H$^+$) (FAB spectra, as a rule); the monoisotopic molar masses are registered in each case. The M+H$^+$ values were rounded up in each case. IR spectra, $^1$H-NMR spectra and UV spectra can also be enlisted for the characterization.

For the working up, the reaction mixture is poured into water, to which sodium chloride and sodium bicarbonate may, where appropriate, have been added, in association with which the reaction products generally precipitate out in crystalline form, frequently only after standing for some length of time. Oily or waxy reaction products are concentrated by extracting, while shaking, with a suitable extracting agent, and then evaporating. If necessary, the reaction products can be fractionated or purified by recrystallization or by chromatography. Intensive digestion in an organic solvent which either does not dissolve the reaction product or else dissolves it as little as possible, for example diethyl ether or cyclohexane, or a mixture of these components, may also frequently suffice for the further purification of the reaction products.

When using carboxylic azolides, the esterification is expediently carried out as a one-pot reaction. In this case, arylacetic acid or hetarylacetic acid, for example, or another carboxylic acid of the formula III [R(5) is OH], is dissolved in absolute pyridine, and a preferably equimolar quantity of N,N-carbonyldiimidazole or N,N-carbonyl[1H-1,2,4-triazole] is added, with the corresponding acid azolides forming at 0° to 20°. After adding an approximately equimolar quantity of corticoid 17-alkyl carbonate of the formula II [R(5)=OH] and a catalytic quantity of a base, preferably sodium hydride or sodium imidazolide, the mixture is stirred in pyridine at between 0° and 40° C., preferably 20°, and then worked up in the customary manner.

However, the carboxylic azolide, which has previously been prepared in absolute tetrahydrofuran with equimolar quantities of N,N'-carbonylazolide and carboxylic acid, and then isolated, can also be added to the steroid dissolved, in solvents such as pyridine, dimethylformamide or tetrahydrofuran, with the subsequent procedure being as described above [see also Chem. Ber. 95, pp. 1284 ff. (1962)].

When esterifying with the aid of phosphonic or phosphinic anhydrides, equimolar quantities of carboxylic acid and corticoid 21-alcohol in absolute pyridine are preferably added to 50% strength propanephosphoric anhydride in methylene chloride at 20° to 60° C., while also adding 4-dimethylaminopyridine as an acid-capturing agent, with the working up being carried out as usual (pouring into ice water, extracting with ethyl acetate, washing with 5% KHSO$_4$, distilling off and crystallizing). Polyphosphoric anhydride (PPA) may also be employed instead of phosphonic anhydrides.

An additional advantageous esterification process, which is applicable to the carboxylic acids according to formula III [R(5) is OH] or included in the list, is the direct reaction of 17-deoxycorticoids of the formula II [R(4) is OH] using water-removing agents such as carbodiimides, preferably N,N'-dicyclohexylcarbodiimide (DCCI). In some cases, "molecular sieves" can also be used as water-removing agents in place of DCCI.

The esterification can be catalytically accelerated or optimized by adding an acid, e.g. sulfuric acid, phosphoric acid, hydrochloric acid, diphenylphosphoric acid or p-toluene sulfonic acid, or their pyridinium salts, or an organic base, such as, for example, dimethylaminopyridine (=particularly advantageous in halogenated solvents, such as, for example, methylene chloride, or in dimethylformamide), something which is very advantageous, particularly in the case of carboxylic acids, e.g. of the indolylacetic acid, pyrrolecarboxylic acid, arylacetic acid and hetarylacetic acid types, etc., which are either sensitive or otherwise only react with difficulty. In this context, it is surprising that the secondary 11-hydroxyl group in the 17-deoxycorticoids which are employed is not practically as a rule esterified simultaneously, as is occasionally observed when esterifying with the corresponding acid halides.

In a particular variant of the process, a catalytic quantity of the pyridinium salt of sulfuric acid is added to a solution of one molar equivalent of 17-deoxycorticoid-21-alcohol [formula II, R(4) is OH] and 1 to 4 molar equivalents, preferably 2 equivalents, of carboxylic acid of the formula III [R(5) is OH] in absolute pyridine, and this is followed, after about 20 min., by the addition of 1 to 4 molar equivalents, preferably 1 to 2 molar equivalents, of dicyclohexylcarbodiimide. The mixture is then stirred at 0° to 50° C., preferably 20° C., until a sample examined by TLC indicates that the starting carboxylic acid has disappeared and that only desired 17-deoxycorticoid-21-carboxylic esters of the formula I are present. The dicyclohexylurea which has formed is filtered off and the filtrate is then expediently poured into water; this is then followed by filtration (in the case of crystal formation) or decantation (in the case of oily or waxy precipitates), washing with water (where appropriate, extraction can also take place with extracting agents, in particular dichloromethane), drying, and recrystallization as usual; alternatively, if required, the reaction products are purified by customary chromatography, preferably on silica gel.

Instead of pyridine, other inert solvents, such as, for example, tetrahydrofuran, dioxane, methylene chloride or dimethylformamide, expediently with the addition of tertiary bases, for example pyridine or 4-dimethylaminopyridine, can also be used in some cases. The latter solvents are to be preferred when molecular sieves are used as water-removing agents.

In addition to this, the following variant has proved valuable for esterifying with the sensitive arylacetic acids and hetarylacetic acids: 1 equivalent of carboxylic acid is dissolved at 0° C. in absolute dichloromethane, and 1 equivalent of DCCI, 0.2 equivalent of 4-N,N'-dimethylaminopyridine and a solution of 1 equivalent of 17-deoxycorticosteroid-21-alcohol in absolute dichloromethane are then added in succession and the mixture is stirred at 20° C. for 18 to 48 hours. After the customary working up, the desired ester of the formula I can be obtained in pure form. A molecular sieve can also be used instead of DCCI.

In a further esterification method, 1 molar equivalent of carboxylic acid and trifluroacetic anhydride are added to 21-deoxycorticoid-21-[tert-butyldimethylsilyl-(O)-ether] in absolute tetrahydrofuran, and the customary working up takes place after stirring at 20° C. for about 1 to 6 hrs. However, the carboxylic acid and the 17-deoxycorticoid-21-alcohol (free form) can also be reacted directly with trifluoroacetic anhydride to give the desired 21-carboxylic ester (=formation of the mixed anhydride from carboxylic acid and trifluoroacetic acid, which anhydride then reacts with the 21-alcohol to give the 21-ester).

Regarding process variant b

A further advantageous process variant, which leads to the corticoids according to the invention, comprises heating a 17-deoxycorticoid-21-halide, preferably 21-iodide or 21-bromide, or 21-sulfonate, preferably 21-p-chlorobenzenesulfonic ester or 21-methanesulfonic ester, with the metal salts, preferably alkali metal salts or trialkylammonium salts, of the carboxylic acids included in list 2, in inert organic solvents, preferably dimethyl sulfoxide, dimethylformamide, 2-butanone, acetone or acetonitrile, at 20° C. up to the boiling points of the solvents used, preferably at about 50° C., for 1 to 16 hrs, preferably 1 to 10 hrs, and isolating after the customary working up, preferably pouring in water, filtering or decanting off the precipitate, and customary purification.

The compounds I prepared according to procedures a) and b) are such that a hydroxyl group in the 11 position can, where appropriate, be oxidized to the keto group by customary methods. This oxidation is preferably carried out using chromium trioxide in an acid medium and in an inert organic solvent. A 9(11) double bond which is present in the corticoid moiety can, where appropriate, be converted by adding hydrohalic acid or by chlorine, in accordance with the usual known methods, into the corresponding 17-deoxycorticoid-21-esters according to the invention having a 11β-hydroxyl, 9α-halide group (9αF, Cl) or 11β,9α-dichloro group.

The process products possess valuable pharmacological properties. They have, in particular, a very strong local and topical antiinflammatory action, and some of them exhibit, surprisingly, a very good ratio of local to systemic antiinflammatory effect, which ratio is often markedly superior, as can be deduced from pharmacological standard tests (see pharmacolog. test part) to that of structurally related corticoid 21-esters, which do not carry any aryl or hetaryl group in the 21-ester radical, such as, for example, 21-ester groups having a 21-alkyl group, and/or to that of analogous 17-deoxycorticoids having an unesterified, thus free 21-hydroxyl group. Accordingly, an agent for treating inflammatory dermatoses and comprising a compound of the formula I is also a subject of the invention.

The process products can be used in veterinary and human therapy in the form of suspensions, ointments, creams, sprays, etc., for treating inflammatory dermatoses of a wide variety of origins. In this context, it is to be emphasized as being particularly advantageous for the local and topical forms of therapy that, owing to their extremely favorable ratio of local to systemic anti-inflammatory effect, even in the case of lengthy therapy at high dosage rates, the process products are able in practice only to elicit trivial systemic side effects. In the case of external treatment, ointments, creams, suspensions, etc. are used at a concentration of 0.01 to 2% by weight. In particular, the process products exhibit a split (ratio) of local/systemic antiinflammatory effects in pharmacological tests which is sometimes appreciably better than that of corresponding preparations having a free 21-hydroxyl group and/or a 21-ester group lacking aryl or hetaryl moieties, as are found in the compounds according to the invention, in the ester moiety. In addition, some of the process products also exhibit a more powerful local antiinflammatory action than do the abovementioned analog preparations. In addition to this, the 17-deoxycorticoid-21-esters according to the invention can often have a still lower atrophoderma-generating effect than do the abovementioned analogous corticoid derivatives, which is a further advantage for their use in dermatotherapeutic treatment.

17-Deoxycorticoid-21-cinnamic esters, in particular those substituted in the 4-position in the aromatic moiety by methoxy, methylenedioxy or ethoxy, and 17-deoxycorticoid-21-[4-(dimethylamino)benzoate] can, by way of their antiinflammatory effect, possess an additional sunscreen effect against solar radiation, in particular UV-B and UV-A radiation.

In addition to this, the process products according to the invention can be combined in pharmaceutical formulations in a manner known per se with diverse antibiotics which are locally active and which are well tolerated by the skin, e.g. of the gentamycin, neomycin, erythromycin or tetracycline type, or of the fusidic acid type, and others. Such combinations of the process products and the locally active antibiotics can be used for treating primary bacterial, or bacterially superinfected, inflammatory dermatoses.

Pharmacological experimental section

Thus, deoxymethasone-21-cinnamate (compound I), for example, exhibited a strong, local antiinflammatory effect while having a markedly diminished systemic effect as compared with that of deoxymethasone, as is evident from the following examples of pharmacological activity.

1. Local antiinflammatory effect in oxazolone ear edema in mice following epicutaneous application.

The method described by Evans, D. P. et al., Br. J. Pharmacol 43, 403 (1971) was used. In mice, 4-ethoxy-methylene-2-phenyl-2-oxazoline (oxazolone) produces an allergic inflammation of the delayed type which can be inhibited by corticosteroids. The experimental animals employed are male NMRI mice of 25 g body weight which are divided into groups of 10 animals each. The animals were sensitized by applying 0.1 ml of a 2% solution of oxazolone in acetone to the shaven skin of the abdomen. On the 9th day following this sensitization, the allergic inflammation was triggered by applying 10 μl of a 2% solution of oxazolone/acetone to the inner side of the right ear auricle (control group). In the treated groups, the abovementioned solution contained the test preparations. 24 hours after applying the solutions, the animals were killed with $CO_2$. A circular sample, measuring 8 mm, was punched out from each of the treated right ear auricle and the untreated left ear auricle. The samples were weighed immediately, with the difference between the right and left auricle weights representing the measure of the degree of inflammation. This inflammatory edematous swelling, in mg, was set to equal 100% in the control group, and the inflammation-inhibiting effect of the preparations is given as the percentage inhibition as compared with the control.

| Treatment | mg/ml | x ± s | Inhibition in % |
|---|---|---|---|
| Control | — | 13.4 ± 3.7 | — |
| Cmpnd. I | 0.03 | 7.7 ± 3.7 | 43 |
| Cmpnd. I | 0.1 | 3.9 ± 2.9 | 71 |
| Cmpnd. I | 0.3 | 2.3 ± 1.3 | 83 |
| Deoxymethasone | 0.03 | 8.6 ± 3.1 | 36 |
| Deoxymethasone | 0.1 | 3.9 ± 3.0 | 71 |
| Deoxymethasone | 0.3 | 2.8 ± 2.3 | 79 |

In both cases, graphic evaulation by the semilogarithmic system gives 50% inhibition values at 0.05 mg/ml, that is equivalence of effect.

2a. Testing for systemic activity following subcutaneous administration in the carrageenin paw edema test in rats The method was described by Winter, C. A. et al. in Proc. Soc. exp. Biol. (N.Y.), 111, 544, (1962). Male Sprague-Dawley rats of approximately 200 g body weight, and in group sizes of n=5, were given the substances subcutaneously (0.2 ml/100 g of body weight, dissolved in sesame oil). Controls were given sesame oil alone. 15 minutes later, 0.1 ml of a 0.5% solution of carrageenin was injected into the left hind paw. Prior to this, and at 3 h and 6 h afterwards, the paw volume was measured (ml) and the increase in swelling was ascertained by comparing with the preliminary value. The numbers are mean value and standard deviation (x±s). Statistical significance was assessed using the Dunnett test.

| Treatment | Dose [mg/kg] | Preliminary value | Increase at 3 h | Increase at 6 h |
|---|---|---|---|---|
| Control | — | 1.43 ± 0.06 | 0.50 ± 0.05 | 0.46 ± 0.07 |
| Cmpnd I | 0.1 | 1.49 ± 0.07 | 0.40 ± 0.06 | 0.39 ± 0.12 |
| Deoxy. | 0.1 | 1.46 ± 0.08 | 0.28 ± 0.16* | 0.23 ± 0.09* |
| Control | — | 1.46 ± 0.10 | 0.69 ± 0.16 | 0.53 ± 0.12 |
| Cmpnd I | 0.3 | 1.51 ± 0.04 | 0.46 ± 0.12 | 0.32 ± 0.05* |
| Deoxy. | 0.3 | 1.43 ± 0.07 | 0.17 ± 0.06* | 0.03 ± 0.03* |

Result: While deoxymethasone already produces a significant effect (*=p<0.05) at 0.1 mg/kg, compound I does not. Even after 0.3 mg has been administered per kg, compound I is still practically without effect whereas deoxymethasone almost completely inhibits the inflammation.

2b. Testing for systemic effect: Gluconeogenesis in rats

Male Sprague-Dawley rats of approximately 140 g in weight were adrenalectomized. They were given an 0.9% solution of sodium chloride as their drinking water. 48 h later, the animals' feed was removed for 24 h. On the day of the experiment (3 days after adrenalectomy and 1 day of starvation), the experimental preparations were administered s.c. (2 ml/kg in sesame oil, with controls only receiving this vehicle). The animals were decapitated 6 h later, with 1 g of liver being removed in each case. The sample was taken up in 5 ml of 0.6M perchloric acid. Following homogenization and centrifugation, glucose was determined in the supernatant. The precipitate (glycogen) was hydrolyzed enzymically with amyloglucosidase, and glucose was also determined in the resulting hydrolysate (hexokinase test kit, from Boehringer Mannheim).

| Treatment | Dose [mg/kg] | Liver glycogen g/100 g of live weight | Liver glyc. + glucose g/100 g of live weight |
|---|---|---|---|
| Control | — | 1.67 ± 0.52 | 14.53 ± 1.95 |
| Cmpnd. I | 0.3 | 1.56 ± 0.50 | 16.91 ± 3.11 |
| Cmpnd. I | 1.0 | 95.86 ± 21.33* | 154.15 ± 4.99* |
| Deoxy. | 0.1 | 38.00 ± 17.43* | 96.55 ± 14.46* |
| Deoxy. | 0.3 | 77.90 ± 29.67* | 137.32 ± 28.04* |

This result demonstrates that while compound I does not have any gluconeogenic effect when administered at 0.3 mg/kg, deoxymethasone already exhibits this undesirable effect when administered at 0.1 mg/kg (=p<0.05, Dunnett's test). Compound I only exhibits this effect when administered at 1 mg/kg, so that the advantage of compound I is to be set at a factor of 3–10.

Overall, the pharmacological test Examples 1–2b demonstrate that while compound I retains a local effect which is of a similar strength to that of deoxymethasone, its undesirable, systemic effect is minimized to a striking degree.

EXAMPLES

The following general comments should be made with regard to the examples given below:

The melting points are measured in a Tottoli apparatus (from Büchi) or on a type 7841 Kofler hot bench from Reichert (Austria), and are not corrected.

The IR spectra (in KBr) are plotted using a Perkin-Elmer 521 grating spectrophotometer. Only the characteristic bands are cited in each case. The UV spectra were plotted (in methanol) using a Beckmann DK 1 A spectrophotometer.

The mass spectroscopic investigations (MS) are mainly carried out using an MS 9 apparatus (from AEI). The MS spectra (molecular weight peak) are chiefly given in: MS=m/z= . . . (M+H$^+$) (measurement using pure isotopes), i.e. the monoisotopic molar mass was registered in each case. FAB-MS spectra were measured as a rule.

Silica gel $F_{254}$ ready-to-use plates (from Merck) were employed for the thin layer chromatography (TLC). Unless otherwise indicated, methylene chloride:methanol=19:1 was used as the eluent (elution distance 7 cm). Development was carried out twice in each case. The spots were either detected at 254 nm using a UV lamp or else rendered visible either by spraying with 10% methanolic sulfuric acid or by heating at 100° C. The $R_F$ values are in every case only relative. 15 silica gel 60, particle size 0.063–0.2 mm (from Merck), was employed for the column chromatography.

When carbonyl chlorides are used in the reactions, absolute dioxane is often advantageously added to the reaction mixture, for example in the case of benzoyl chloride where the ratio of dioxane/pyridine is about 1:1, and, in order to accelerate the reaction, the reaction mixture is often, particularly in the case of sterically hindered or less reactive carbonyl chlorides or carboxylic anhydrides, heated at about 60° C. (monitoring of the course of the reactions using TLC).

The reaction products can be characterized by thin layer chromatography (TLC); in this context, the reaction products have $R_F$ values of about 0.65–0.75. As a rule, the reaction products are characterized by mass spectra using MS=m/z= . . . (M+H$^+$) (FAB spectra as a rule); the monoisotopic molar mass is registered in each case. The M+H$^+$ values were rounded up in each case. IR, $^1$H-NMR and UV spectra can also be enlisted for the characterization.

Example 1

Deoxymethasone 21-(3-phenyl)propionate a) A solution of 1.8 g of 3-phenylpropionyl chloride (~0.0011 mol) in 10 ml of absolute dioxane is added dropwise, at 0° C. and while stirring, to a solution of 3 g of deoxymethasone (~0.008 mol) in 20 ml of absolute pyridine. After 5 to 6 hrs of stirring at 0° C. (TLC indicates completed formation of the desired reaction product), the mixture is poured into 500 ml of a half-saturated, aqueous solution of sodium chloride, and the precipitate (oily or wax) is isolated by way of a pleated filter; this precipitate is dissolved in methylene chloride (or ethyl acetate), and this solution is washed with water and dried using sodium sulfate; the solvent is distilled off in vacuo and the product is crystallized with diethyl ether or diisopropyl ether or petroleum ether, filtered off and recrystallized, where appropriate, from ethanol/diethyl ether (where appropriate adding diisopropyl ether or petroleum ether). 3.9 g (96.0%) of the abovementioned title compound are obtained with a m.p. of 161° C.

MS: m/z=509 (M+H$^+$)

TLC: $R_F$=0.6 b) The same reaction product, having the same data, as described in Example 1a) is obtained if 3.1 g of 3-phenylpropionic anhydride are employed in Example 1a) in place of 3-phenylpropionyl chloride and the reaction, and the working up and purification are carried out in the same manner as described in Example 1a).

c) 1.8 g of 3-phenylpropionyl chloride are added dropwise, in portions, at 0° C. and while stirring, to a solution of 3 g (0.008 mol) of deoxymethasone in 25 ml of absolute acetone and 10 ml of absolute pyridine. The mixture is left stirring at room temperature (21° C.) for 20 hrs and is then heated, if a thin layer chromatogram still detects starting material, for a few more hours (approximately 5 hrs) at 40° to 50° C.; it is then allowed to cool down and is poured into 60 ml of a half-saturated, aqueous solution of sodium chloride; the aqueous phase is decanted from the precipitated oil or wax (if crystals precipitate out, these are filtered off) and the precipitate is taken up in methylene chloride; the organic phase is washed with water and dried, for example with sodium sulfate, and the solvent is distilled off. The residue which remains is recrystallized from ethanol, methylene chloride (dissolution), with the addition of diethyl ether or diisopropyl ether, yielding 3.2 g of the abovementioned title compound, m.p. 158° to 160° C.

In TLC (eluent: $CH_2Cl_2:CH_3OH=19:1$), this compound, and also the abovementioned precipitate, still exhibit subsidiary spots in addition to the main spot at F≅0.6. For final purification (TLC), chromatography is carried out on silica gel [particle size 0.063 to 0.2000 mm (Merck AG), 20×3 cm column] using methylene chloride/methanol=998:2 (50 ml fractions). The fractions which are found by subsequent TLC to have an RF value of approximately 0.6 are combined. After the eluent has been distilled off, 2.0 g (in the best replicate mixture 2.8 g) of crystalline title compound with an m.p. of 160° C. are obtained following crystallization from diethyl ether and/or ethanol, methylene chloride and diethyl ether (or diisopropyl ether).

MS: m/z=509 (M+H$^+$)

TLC: $R_F$≅0.6 (SC=0.4) (SC=starting compound)

The oily or waxy, oily precipitate mentioned above also gives the MS data after drying of m/z=509 (M+H$^+$)

Example 2

Deoxymethasone 21-phenoxyacetate

In the same manner as described in Example 1a), 3 g of deoxymethasone are reacted with 1.8 g of phenoxyacetyl chloride in place of the 3-phenylpropionyl chloride, and the product is worked up and isolated and the title compound is obtained in pure crystalline form (possibly also in amorphous form). 3.82 g of the abovementioned title compound are obtained. m.p. 147° C.

MS: m/z=511 (M+H$^+$) TLC: $R_F$≅0.7

Example 3

Deoxymethasone 21-phenylacetate a) In the same manner as described in Example 1a), 3 g of deoxymethasone are reacted with 1.75 g of phenylacetyl chloride in place of the 3-phenylpropionyl chloride, and the product is worked up and isolated and the title compound is obtained in pure crystalline form (crystallized; possibly also in amorphous form). 2.7 g of the abovementioned title compound are obtained. m.p. 151° to 153° C.

MS: m/z=495 (M+H$^+$)

TLC: $R_F$≅0.7 b) A freshly prepared mixture of 250 mg of concentrated sulfuric acid in 4 ml of absolute pyridine (suspension of pyridinium sulfate) is added, at 20° C. and while stirring, to a solution of 6.3 g of deoxymethasone and 8.65 g of phenylacetic acid (dried for 5 hrs.+in vacuo over $P_2O_5$ at approximately 50° to 60° C.) in 44 ml of absolute pyridine. 5.1 g of N,N'-dicyclohexylcarbodiimide are added after the mixture has been stirred for 15 min. A crystalline precipitate of the N,N'-dicyclohexylurea which has been formed soon precipitates out of the initially clear solution. The mixture is stirred until TLC fails to detect any further starting compound and, instead, can detect the reaction product at F≅0.7 (as a rule, a reaction time of 16 hours; a longer reaction time, for example standing or stirring over the weekend, does not have any adverse effect on the reaction result). After this, 2.2 ml of acetic acid or acetic anhydride are added and the mixture is left to stand for a further 1 hr at 20° C. and then for 24 to 48 hrs in a deep freeze (approximately −15° C.). The precipitated N,N'-dicyclohexylurea is filtered off and washed with pyridine which is cooled to approximately −15° C.; the filtrate is then stirred into approximately 500 ml of a half-saturated, aqueous solution of sodium chloride, and approximately 5 ml of ethanol are added; the oily-crystalline precipitate is then filtered off, washed several times with water and then taken up in approximately 100 ml of methylene chloride. After this solution has been dried with sodium sulfate, the solvent is distilled off and the residue is crystallized by adding diethyl ether. Deoxymethasone 21-phenylacetate is obtained with an m.p. of 132° to 145° C. and can be recrystallized from tert-butanol/diethyl ether. m.p.: 156° C. (yield 4.0 g)

MS: m/z=495 (M+H$^+$)

TLC: $R_F$≅0.7 ($R_F$ of SC≅0.4)

c) A further reaction mixture is prepared which is analogous to that described in Example 3b); however, the acidic catalyst, concentrated sulfuric acid in pyridine, is omitted. After a reaction time which is approximately five times longer than that given in Example 3b), a TLC sample indicates that starting compound is no longer present. After a working up and purification which are analogous to those described in Example 3b), deoxymethasone 21-phenylacetate is obtained having the same characteristics as given in Example 3b).

The title compound is also obtained with the same data if absolute dimethylformamide is used as the solvent in place of pyridine.

d) A further reaction mixture is prepared which is analogous to that described in Example 3b). However, 250 mg of p-toluenesulfonic acid are added in place of the sulfuric acid. After a working up and purification which are analogous to those described in Example 3b), deoxymethasone 21-phenylacetate is obtained having the same characteristics as given in Example 3b).

Example 4

Deoxymethasone 21-(indole-3-acetic)ester

Pyridinium sulfate (comprising 56 mg of conc. sulfuric acid in 2.5 ml of absol. pyridine, in accordance with Example 2b) is added, at 20° and while stirring, to a solution of 1.92 g of deoxymethasone and 3.1 g of 3-indoleacetic acid (dried) in 15 ml of absolute pyridine. 1.55 g of N,N'-dicyclohexylcarbodiimide are added after the mixture has been stirred for 30 minutes (20° C.). After the mixture has been stirred at 20° C. for 48 hours, the mass spectrum indicates a m/z=534.2 (M+H$^+$), and no longer indicates m/z=377 (M+H$^+$) for the starting steroid. After further treatment and working up which are analogous to those described in Example 3 b), an oily precipitate, which turns into a wax, is obtained after the mixture has been poured into approximately 500 ml of a half-saturated solution of sodium chloride. The wax is decanted or filtered off, washed with water and dried in vacuo over $P_2O_5$ in a desiccator. After grinding with petroleum ether, 1.35 g of the title compound are obtained as an amorphous product.

MS (of wax or amorphous material): m/z=534 (M+H$^+$)

TLC≅0.75 (main spot=main spot+a few weak subsidiary spots). For the final purification, chromatography takes place on silica gel using methylene chloride/methanol=99.5:0.5 (column: diameter=5 cm; h=20 cm). The resulting eluate fractions which have an $R_F$≅0.75 are pooled and freed of solvents by distillation. The residue is crystallized from diethyl ether. 1.0 g of the title compound is obtained, which title compound has a m.p. of ~160° C. and the same MS and TLC data as the waxy or amorphous title compound.

MS: m/z=534 (M+H$^+$)

TLC: $R_F$≅0.75

Example 5

Deoxymethasone 21-cinnamic ester

A solution of 3.5 g of cinnamoyl chloride in 20 ml of absolute dioxane is added dropwise, at 0° C. and while stirring, to a solution of 6 g of deoxymethasone in 40 ml of absolute pyridine. After the mixture has been stirred at 0° C. for 5 hrs (TLC indicates complete formation of the desired reaction product), it is poured into 1 l of a half-saturated, aqueous solution of sodium chloride; the precipitate (wax) is isolated using a pleated filter and taken up in methylene chloride (or ethyl acetate); this solution is washed with water and dried with sodium sulfate, and the solvent is distilled off in vacuo; the product is crystallized using diethyl ether or diisopropyl ether or petroleum ether, filtered off and recrystallized, where appropriate, from ethanol/diethyl ether (where appropriate adding diisopropyl ether or petroleum ether). 7.5 g of the abovementioned title compound are obtained with an m.p. of 161° C.

MS: m/z 507 (M+H$^+$)

TLC: $R_F$≅0.7

Example 6

Corticosterone 21-cinnamic ester

In the same manner as described in Example 5, 580 mg of corticosterone in 4 ml of absol. pyridine are reacted with 350 mg of cinnamoyl chloride in 2 ml of absol. dioxane; after the mixture has been stirred at 0° C. for 5 hours, it is worked up (poured into 100 ml of a half-saturated solution of sodium chloride, etc.), and the product is prepared (isolated) by crystallization. 660 mg of the abovementioned title compound are obtained with a m.p. of 154°–157° C.

MS: m/z=477 (M+H$^+$)

TLC: $R_F$≅0.7

Example 7

11-deoxycorticosterone 21-cinnamic ester 570 mg of 11-deoxycorticosterone, in place of the corticosterone, are reacted in the same manner as described in Example 6; the mixture is then worked up and the product is isolated. 520 mg of the abovementioned title compound are obtained with a m.p. of 140°–143° C.

MS: m/z=461 (M+H$^+$)

TLC: $R_F$≅0.75

Example 8

Fluocortolone 21-cinnamic ester

In the same manner as described in Example 5, 600 mg of fluocortolone in 4 ml of absol. pyridine are reacted with 350 mg of cinnamoyl chloride in 2 ml of absol. dioxane (0° C., 5 hrs), and the mixture is then worked up (pouring into 100 ml of a half-saturated solution of sodium chloride, etc.), and the product is isolated in crystalline form. 720 mg of the abovementioned title compound are obtained with a m.p. of 154°–159° C.

MS: m/z=507 (M+H$^+$)

TLC: $R_F$≅0.8

Example 9

Diflucortolone 21-cinnamic ester 610 mg of diflucortolone, in place of the fluocortolone, are reacted in the same manner as described in Example 8; the mixture is worked up, and the product is isolated. 560 mg of the abovementioned title compound (m.p. 120°–128° C.; amorphous) are obtained from diisopropyl ether (grinding).

MS: m/z=525 (M+H$^+$)

TLC: $R_F$≅0.8

Example 10

Clocortolone 21-cinnamic ester 620 mg of clocortolone, in place of the fluocortolone, are reacted in the same manner as described in Example 8; the mixture is then worked up and the product is isolated. 590 mg of the abovementioned title compound (amorphous) are obtained from diisopropyl ether (grinding).

MS m/z=542 (M+H$^+$)

TLC: $R_F$≅0.8

Example 11

9α-fluorocorticosterone 21-cinnamic ester 600 mg of 9α-fluorocorticosterone, in place of the fluocortolone, are reacted in the same manner as described in Example 8; the mixture is then worked up and the product is isolated. 630 mg of the abovementioned title compound are obtained in amorphous form from n-hexane (grinding).

MS: m/z=495 (M+H$^+$)

TLC: $R_F$≅0.8

Example 12

Deoxymethasone 21-(4-methoxycinnamic) ester

A solution of 4.2 g of 4-methoxycinnamoyl chloride in 20 ml of absolute dioxane is added dropwise, at 0° C. and while stirring, to a solution of 6 g of deoxymethasone in 40 ml of absolute pyridine. After the mixture has been stirred at 0° C. for 5 hrs (TLC indicates complete formation of the desired reaction product), it is poured into 1 l of a half-saturated, aqueous solution of sodium chloride, and the precipitate (wax) is isolated using a pleated filter; this precipitate is taken up in methylene chloride (or ethyl acetate), and this solution is washed with water and dried with sodium sulfate, and the solvent is distilled off in vacuo; the product is crystallized with diethyl ether or diisopropyl ether or petroleum ether, and then filtered off and, where appropriate, recrystallized from ethanol/diethyl ether (where appropriate adding diisopropyl ether or petroleum ether). 9.4 g of the abovementioned title compound are obtained with a m.p. of 185° C. In a further reaction mixture, the reaction product had an m.p. of 194° C.

MS: m/z=537 (M+H$^+$)

TLC: R$_F$≅0.75

In a further reaction mixture, the reaction product had a melting point of 194° C.

Example 13

Corticosterone 21-(4-methoxycinnamic)ester

In the same manner as described in Example 12, 580 mg of corticosterone in 4 ml of absol. pyridine are reacted with 420 mg of 4-methoxycinnamoyl chloride in 2-ml of absol. dioxane, and, after it has been stirred at 0° C. for 5 hours, the mixture is worked up (pouring into 100 ml of a half-saturated solution of sodium chloride, etc.) and the product is prepared (isolated) by crystallization. 620 mg of the abovementioned title compound are obtained with an m.p. of ~160° C.

MS: m/z=507 (M+H$^+$)

TLC: R$_F$≅0.7

Example 14

Deoxycorticosterone 21-(4-methoxycinnamic) ester 570 mg of deoxycorticosterone, in place of the deoxymethasone, are reacted in the same manner as described in Example 12; the mixture is worked up and the product is isolated. 500 mg of the abovementioned title compound are obtained with a m.p. of 153° C.

MS: m/z=491 (M+H$^+$)

TLC: R$_F$≅0.75

Example 15

Fluocortolone 21-(4-methoxycinnamic) ester

In the same manner as described in Example 12, 600 mg of fluocortolone in 4 ml of absol. pyridine are reacted with 420 mg of 4-methoxycinnamoyl chloride in 2 ml of absol. dioxane (0° C., 5 hrs), and the mixture is worked up (pouring into 100 ml of a half-saturated solution of sodium chloride, etc.) and the product is isolated in crystalline form. 690 mg of the abovementioned title compound are obtained with a m.p. of 164°–176° C. (previously from 150° C., sintering, amorphous).

MS: m/z=537 (M+H$^+$)

TLC: R$_F$≅0.75

Example 16

Diflucortolone 21-(4-methoxycinnamic) ester 610 mg of diflucortolone, in place of the fluocortolone, are reacted in the same manner as described in Example 15; the mixture is then worked up and the product is isolated. 590 mg of the abovementioned title compound (amorphous) are obtained from diisopropyl ether (grinding).

MS: m/z=555 (M+H$^+$)

TLC: R$_F$≅0.8

Example 17

Clocortolone 21-(4-methoxycinnamic) ester 620 mg of clocortolone, in place of the fluocortolone, are reacted in the same manner as described in Example 15; the mixture is then worked up and the product is isolated. 620 mg of the abovementioned title compound (amorphous) are obtained from diisopropyl ether (grinding).

MS: m/z=572 (M+H$^+$)

TLC: R$_F$25 0.8

Example 18

9α-Fluorocorticosterone 21-(4-methoxycinnamic) ester 600 mg of 9α-fluorocorticosterone, in place of the fluocortolone, are reacted in the same manner as described in Example 15; the mixture is then worked up and the product is isolated. 680 mg of the abovementioned title compound (amorphous) are obtained from diisopropyl ether (grinding).

MS: m/z=525 (M+H$^+$)

TLC: R$_F$≅0.8

Example 19

Deoxymethasone 21-(4-phenyl)cinnamic ester 96 mg of 4-dimethylaminopyridine and 2.0 g of dicyclohexylcarbodiimide are added, at 0° C. and while stirring, to a solution of 3.0 g of deoxymethasone and 2.3 g of 4-phenylcinnamic acid in 60 ml of absol. methylene chloride. The reaction solution, which is initially clear, soon becomes turbid. After the mixture has been stirred at room temperature for approximately 6 hours, a TLC sample indicates that starting compound is no longer present. The mixture is then stored at +4° C. for 2 days and at –15° C. (deep freeze) for 2 days, after which the precipitated dicyclohexylurea is filtered off and washed with a little methylene chloride which is cooled to –15° C.; the organic solvent is then stripped off in vacuo. The residue which remains is crystallized from boiling diethyl ether and, where appropriate, recrystallized from ethanol/diethyl ether. 4.1 g of the abovementioned title compound are obtained with a m.p. of 142° C.

MS: m/z=583 (583.3)–(M+H$^+$)

TLC: R$_F$≅0.75

Example 20

Deoxymethasone 21-(trans-3,4-methylenedioxy) cinnamic ester

In the same manner as described in Example 19, 3 g of deoxymethasone are reacted with 2.0 g of trans-3,4-methylenedioxycinnamic acid in place of the 4-phenylcinnamic acid, and the mixture is worked up and the product is isolated and prepared in pure form. 1.9 g of the abovementioned title compound are obtained; m.p. 147°–151° C.

MS: m/z=551 (M+H$^+$)

TLC: R$_F$≅0.7

Example 21

Deoxymethasone 21-(trans-3,4-dimethoxy)cinnamic ester

In the same manner as described in Example 19, 3 g of deoxymethasone are reacted with 2.0 g of trans-3,4-dimethoxycinnamic acid in place of the 4-phenylcinnamic acid, and the mixture is worked up and the product is isolated and prepared in pure form. 2.4 g of the abovementioned title compound are obtained with a m.p. of 139°–144° C.

MS: m/z=567 (M+H$^+$)

TLC: R$_F$≅0.75

If, in Example 21, an equivalent quantity of trans-2,3-dimethoxycinnamic acid or trans-2,4-dimethoxycinnamic acid or trans-2,5-dimethoxycinnamic acid or trans-3,5-dimethoxycinnamic acid is employed in the reaction in place of 2.0 g of trans-3,4-dimethoxycinnamic acid, this then results, after analogous conduct of the reaction, working-up and isolation, in the corresponding deoxymethasone 21-trans-2,3- (or 2,4-, or 2,5-, or 3,5-, respectively) dimethoxycinnamic ester, all with MS: m/z=567 (M+H$^+$).

Example 22 (p denotes 4)

Deoxymethasone 21-(p-methylcinnamic) ester

In the same manner as described in Example 19, 3 g of deoxymethasone are reacted with 1.9 g of p-methylcinnamic acid in place of the 4-phenylcinnamic acid, after which the mixture is worked up and the product is isolated and prepared in pure form. 2.1 g of the abovementioned title compound are obtained; m.p. 171° C.

MS: m/z=521 (M+H$^+$)

TLC: R$_F$≅0.7

Example 23

If, in Example 22, 1.9 g of α-methylcinnamic acid (=C$_6$H$_5$CH=C(CH$_3$)CO$_2$H) is employed in the reaction in place of p- or 4-methylcinnamic acid, this then results, after analogous conduct of the reaction, working-up and isolation, in the isomeric deoxymethasone 21-(α-methylcinnamic) ester (amorphous crystalline crop after precipitating with diethyl ether).

MS: m/z=521 (M+M$^+$)

TLC: R$_F$≅0.75

If, in Example 22, an equivalent quantity (1.9 g) of β-methylcinnamic acid (e.g. trans-methylcinnamic acid) is employed in the reaction in place of α-methylcinnamic acid, this then results in the deoxymethasone 21-(β-methylcinnamic)ester.

Example 24

Deoxymethasone 21-phenylpropiolic ester

In the same manner as described in Example 19, 3 g of deoxymethasone are reacted with 1.9 g of phenylpropiolic acid in place of the 4-phenylcinnamic acid (reaction time, 24 hrs); the mixture is worked up and the product is isolated. The abovementioned title compound slowly crystallizes out, in crystalline form, which can only be finally purified with difficulty, from the resulting dark oil (2.2 g) after several days. Measurements on the oily/crystalline crude product:

MS: m/z=505 (M+H$^+$)

TLC: R$_F$=0.8

Example 25

Deoxymethasone 21-(5-phenyl-2,4-pentadienoic) ester

In the same manner as described in Example 19, 3 g of deoxymethasone are reacted with 1.6 g of 5-phenyl-2,4-pentadienoic acid (=cinnamylideneacetic acid) in place of the 4-phenylcinnamic acid, after which the mixture is worked up and the substance is isolated and prepared in pure form. 3.1 g of the abovementioned title compound are obtained with a m.p. of 140°–146° C. (indistinct).

MS: m/z=533 (M+H$^+$)

TLC: R$_F$≅0.75

Example 26

Deoxymethasone 21-[4-(4-(N,N)-(bis(2-chloroethyl)amino)phenyl)butyrate]

Pyridinium sulfate (comprising 300 mg of conc. sulfuric acid in 10 ml of absol. pyridine, prepared in accordance with Example 2b) is added, at 20° C. and while stirring, to a solution of 8.0 g of deoxymethasone and 7.2 g of 4-(4-(N,N)-(bis(2-chloroethyl)amino)phenyl)butyric acid (=chlorambucil) in 50 ml of absol. pyridine. 5.77 g of N,N-dicyclohexylcarbodiimide are added after the mixture has been stirred at 20° C. for 20 minutes. 2 ml of glacial acetic acid are then added after the mixture has been stirred at 20° C. for 48 hrs, and this mixture is then left in a deep freeze (–15° C.) for 48 hrs. The precipitated N,N'-dicyclohexylurea (6.1 g) is then filtered off, and approximately 300 ml of a half-saturated, aqueous solution of sodium chloride are added to the filtrate, whereupon an oil separates out. The oil is filtered off using a pleated filter and treated with 400 ml of water, following which it turns into a wax within the course of 48 hrs. The wax is filtered off, washed with water and dried, for the last time in a vacuum desiccator. It is dissolved under reflux in boiling isopropanol, and this solution is allowed to cool to 20° C., whereupon a thick crop of crystals soon precipitates out. This crop is filtered off and washed with isopropanol which has been cooled to 0° C. Drying results in 6.2 g of the abovementioned title compound with a m.p. of 142° to 145° C.; (another reaction mixture gives a m.p. of 160°–168° C.: the preparation evidently has a double or multiple melting point (polymorphic!))

MS: m/z=662 (M+H$^+$)

TLC: R$_F$≅0.8

Example 27

Deoxymethasone 21-[3-(3-furyl)acrylic ester]

A solution of 254 mg of 3-furylacryloyl chloride (1.6 mmol) in 2 ml of absolute dioxane is added dropwise, at 0° C. and while stirring, to a solution of 500 mg of deoxymethasone (1.3 mmol) in 3 ml of absolute pyridine. After the mixture has been stirred for 4 hours at 0° C. and has been left to stand for 62 hours (=over the weekend) in a refrigerator at +4° C. (TLC indicates complete formation of the desired reaction product; F≅0.8 (deoxymethasone has≅0.6)), the precipitate (=pyridinium hydrochloride) which has separated out is filtered off at +4° C. The solvents contained in the resulting filtrate are to a large extent distilled off under high vacuum. The resulting residue is ground with diethyl ether, and the resulting crystalline crop is filtered off and washed several times with diethyl ether. If desired, the resulting crystalline crop can be recrystallized from ethanol/diethyl ether (where appropriate, adding dichloromethane for complete dissolution). 580 mg of the abovementioned title compound are obtained with a m.p. of 216° C.

MS: m/z=497 (M+H$^+$)

TLC: R$_F$≅0.8

The synthesis of the isomeric compounds deoxymethasone 21-[3-(2-thienyl)acrylic ester] and deoxymethasone 21-[3-(2-furyl)acrylic ester] is expediently achieved proceeding from the free acid reagents 2-thienylacrylic acid and 2-furylacrylic acid, respectively (in place of the 4-phenylcinnamic acid), and carrying out the reaction in accordance with Example 19.

Example 28

Deoxymethasone 21-[3-(3-thienyl)acrylic ester]

In the same manner as described in Example 27, 0.5 g of deoxymethasone are reacted with 2.75 mg of 3-thienylacryloyl chloride in place of the acid chloride used in that example; the mixture is worked up in an analogous manner and the product is prepared in pure form by crystallization. 580 mg of the abovementioned title compound are obtained from diethyl ether. m.p.: 219° C.

MS: m/z=513 (M+H$^+$);

TLC: R$_F$≅0.8

The examples in Tables 1 and 2 below, where R(1)' is the entire side chain on the 21CH$_2$O group, are analogous to the above examples.

It was only the molecular weight peaks (m/z=. (M+H$^+$)), obtained from the mass spectra, which were in each case evaluated (as oil or wax or in amorphous form or crystallized) for characterizing the synthesis products, and this was not, as a rule, followed by any purification by crystallization (recrystallization) or chromatography.

TABLE 1

Basic corticoid: deoxymethasone

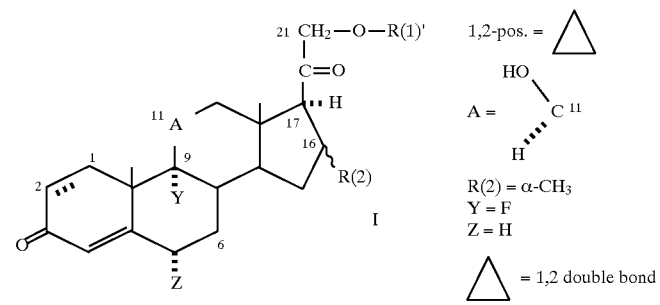

| Run No. | Carboxylic acid or carbonyl chloride employed | Process variant according to Example | R(1)' | MS (m/z) (M + H$^+$) |
|---|---|---|---|---|
| 1.1 | Ph—SCH$_2$CO$_2$H | 3 b | Ph—SCH$_2$CO— | 527 |
| 1.2 | Ph—(CH$_2$)$_3$CO$_2$H | 3 b | Ph—(CH$_2$)$_3$CO— | 523 |
| 1.3 | Pyridyl—CH$_2$CO$_2$H | 3 b, 4 | Pyridyl—CH$_2$CO— | 496 |
| 1.4 | Pyridyl—CH=CH—CO$_2$H | 4 | Pyridyl—CH=CH—CO— | 508 |

TABLE 2

Basic corticoid: deoxymethasone

Structure I: Steroid framework with position 21 $CH_2-O-R(1)'$, C=O at C-20, H at C-17, R(2) at C-16, Y at C-9, Z at C-6; A group at C-11.

1,2-pos. = △ (1,2 double bond)

$A = \begin{array}{c} HO \\ \diagdown \\ C^{11} \\ \diagup \\ H \end{array}$

R(2) = α-$CH_3$
Y = F
Z = H

△ = 1,2 double bond

| Run No. | Carboxylic acid or carbonyl chloride employed | Process variant according to Example | R(1)' | MS (m/z) (M + H$^+$) |
|---|---|---|---|---|
| 2.1 | 3-thienyl-$CH_2CO_2H$ | 3 b | 3-thienyl-$CH_2CO-$ | 501 |
| 2.2 | 2-thienyl-$CH_2CH_2COCl$ | 1 a, 5 | 2-thienyl-$CH_2CH_2CO-$ | 515 |
| 2.3 | 2-furyl-$CH_2CH_2COCl$ | 1 a, 5 | 2-furyl-$CH_2CH_2CO-$ | 515 |
| 2.4 | 2-methylindol-3-yl-$CH_2-CO_2H$ | 3 b, 4 | 2-methylindol-3-yl-$CH_2-CO-$ | 548 |
| 2.5 | 5-methoxyindol-3-yl-$CH_2-CO_2H$ | 3 b, 4 | 5-methoxyindol-3-yl-$CH_2-CO-$ | 564 |
| 2.6 | 2-naphthyl-$CH_2-CO_2H$ | 3 b | 2-naphthyl-$CH_2-CO-$ | 545 |
| 2.7 | indol-3-yl-$CH=CH-CO_2H$ | 4 | indol-3-yl-$CH=CH-CO-$ | 546 |

A) The following carboxylic acids of the formula III [R(5)=OH], or their activated derivatives, are examples of suitable starting compounds (the aryl and/or hetaryl groups therein correspond to the substituents R(I)):

a.) Non-fused acids

Phenylacetic acid; 2-methyl- or 3-methyl- or 4-methylphenylacetic acid, 4-tert-butylphenylacetic acid; 2-chloro- or 3-chloro- or 4-chlorophenylacetic acid; 2,6-dichloro- or 3,4-dichlorophenylacetic acid; 2-fluoro- or 3-fluoro- or 4-fluorophenylacetic acid; 2,6-difluorophenylacetic acid; 2-nitro- or 3-nitro- or 4-nitrophenylacetic acid; 2,4-dinitrophenylacetic acid; 2-methoxy- or 3-methoxy- or 4-methoxyphenylacetic acid; 4-benzyloxyphenylacetic acid; 3-chloro-4-methoxyphenylacetic acid; 3-bromo-4-methoxyphenylacetic acid; 3-nitro-4-methoxyphenylacetic acid; 3,4-dimethoxyphenylacetic acid; 2,3,4-trimethoxyphenylacetic acid; 3,4-methylenedioxyphenylacetic acid; 3,4- diethoxyphenylacetic acid; 4-biphenylacetic acid; 3-phenoxyphenylacetic acid; 2-acetamino- or 3-acetamino- or 4-acetaminophenylacetic acid; 3-(N)-BOC-aminophenylacetic acid; 4-formylaminophenylacetic acid; 4-N,N-dimethylaminophenylacetic acid;

4-Benzyloxyphenylacetic acid; 4-(2-methoxybenzyloxy)phenylacetic acid; 4-(4-fluorobenzyloxy)phenylacetic acids; 2-(thiazol-4-yl)acetic acid; 2-(thiazol-4-yl)-2-methoxyiminoacetic acid;

3-phenylpropionic acid; D,L-2-phenylpropionic acid; 3-[4-methylphenyl]propionic acid, 3-[4-chloro- or 4-fluoro- or 4-methoxyphenyl]propionic acids; (S)-(+)-2-phenylpropionic acid; (R)-(−)-2-phenylpropionic acid; 4-phenylbutyric acid; phenoxyacetic acid and derivatives (substituents in the phenyl moiety); cis- or (preferred) trans-cinnamic acid; 2-, 3- or 4-methoxycinnamic acid; 4-ethoxycinnamic acid; 3,4-dimethoxycinnamic acid; 3,4,5-trimethoxycinnamic acid; 4-fluorocinnamic acid; 3- or 4-chlorocinnamic acid; 3-bromocinnamic acid; 2- or 3-nitrocinnamic acid; 4-cyanocinnamic acid; 4-isopropylcinnamic acid; 4-tert-butylcinnamic acid, 2- or 4-trifluoromethylcinnamic acid; D,L- or (S)- or (R)-2-(4-isobutylphenyl)propionic acid (Ibuprofen); 4-(isobutylphenyl)-acetic acid (Ibufenac); phenylmercaptoacetic acid; phenylpropiolic acid; 2-methyl-3-(4-tetradecyloxyphenyl)-2-propenoic acid (MTPA); 3-(4-crotyloxyphenyl)propionic acid; 4-dodecylbenzoylacetic acid (DBAA); benzoylacrylic acid; chlorambucil; 3,4,5-trimethoxybenzoylacrylic acid; 2-(4-(thiazol-2-yl)phenyl)propionic acid; 2-(xanthonoxy)acetic acid; 2-phenylcyclopropanecarboxylic acids (trans); 3-(phenylmercapto)acrylic acid; (4-phenyl)butyric acid;

2-thienylacetic acid; 3-thienylacetic acid; 1- or 2-furylacetic acid; 2-, 3- or 4-pyridylacetic acid; 2-mercaptomethylnicotinic acid;

3-(2- or 3-Furyl)acrylic acid; 3-(2-thienyl)acrylic acid; 3-(3-thienyl)acrylic acid; 3-(4- or 2-pyridyl)acrylic acid; 3-(2-thienyl)propionic acids; 3-(2-furyl)propionic acid; 3-(4-imidazolyl)acrylic acid; (N-methylpyrrol-2-yl)acetic acid;

b.) Fused acids

3-Indolylacetic acid; 2-indolylacetic acid; (N-methyl)-2- or -3-indolylacetic acid; 3-(3-indolyl)propionic acid; 3- or 2-indolylacrylic acid (also (N-methyl)); (2-methyl-3-indolyl)acetic acid, 3,4-(methylenedioxy)phenylacetic acid; 3,4-(methylenedioxy)cinnamic acid; indole-3-butyric acid; (5-methoxyindol-3-yl)acetic acid; naphthyl-1- or -2-acetic acid; flavone-8-acetic acid; 5,6-dimethylxanthone-4-acetic acid (L. L. Thomsen et al.: Cancer Chemother, Pharmacol. 31, 151ff. (1992) demonstrate that the corticoid 21-carboxylic esters prepared from this could also have an antitumorigenic effect, likewise the abovementioned chlorambucil).

We claim:

1. A 17-deoxycorticoid-21-dicarboxylic ester of the formula I in which:

A is CHOH, CH$_2$, or C=O;

X is (C$_2$–C$_4$) aliphatic hydrocarbon, unsaturated once or more than once;

Y is hydrogen, fluorine or chlorine;

Z is hydrogen, fluorine or methyl;

R(1) is optionally substituted or fused aryl or hetaryl; and

R(2) is hydrogen or α-methyl or β-methyl.

2. A 17-Deoxycorticoid-21-carboxylic ester as claimed in claim 1 in which:

R(1) is defined as in claim 1;

A is CHOH (in the β configuration);

Y is F;

Z is hydrogen;

R(2) is α-methyl.

3. A pharmaceutical composition comprising an effective amount of a compound of the formula I as claimed in claim 1, together with a pharmaceutically acceptable carrier.

4. A process for treating dermatoses comprising applying to an affected skin site an effective amount of a compound of the formula I as claimed in claim 1, combined with a pharmaceutically acceptable carrier.

5. A process for preparing a compound of the formula I as claimed in claim 1, comprising:

a) reacting a compound of the formula II, in which R(4) is OH and the remaining substituents are as defined in claim 1;

a1) with an activated carboxylic acid of the formula III,

R(5)-CO—X-R(1)    III in which

X and R(1) are as defined in claim 1, and

R(5) is Cl, Br, O[—CO—X—R(1)]-, or —OC—(O)CF$_3$; or a2) with a carboxylic acid of the formula III,

R(5)-CO—X—R(1)    III in which

R(5) is OH and the other substituents are as defined in claim 1; in the presence of a water-eliminating reagent, or b) reacting a compound of the formula II

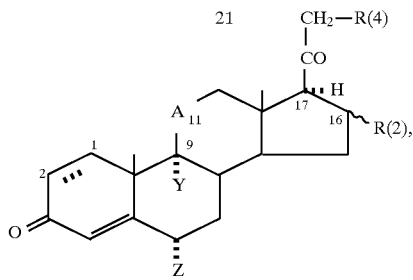

in which R(4) is Br, I, or a sulfonic aryl ester group or sulfonic alkyl ester group, and the other substituents are as defined in claim 1, with a salt of a carboxylic acid of the formula III,

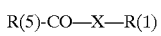

in which

R(5) is —(O—Me$^+$) and the other substituents are as defined in claim 1.

6. The process as claimed in claim 5 wherein said activated carboxylic acid of the formula III is a halide, anhydride or azolide.

7. The process as claimed in claim 5 wherein R(5) is an activated acid radical.

8. The process as claimed in claim 5 wherein said water-eliminating reagent is DCCI.

9. The process as claimed in claim 5 wherein said salt reacted with said compound of the formula II is a K salt, Na salt or a trialkylammonium salt.

10. The process as claimed in claim 5 wherein said Me$^+$ in R(5) is the cation of an alkali metal salt or a trialkylammonium salt.

11. A 17-Deoxycorticoid-21-carboxylic ester as claimed in claim 1 in which R(1) is optionally substituted aryl, arylalkyl, arylthioalkyl, pyridyl, pyridylalkyl, thienyl, thienylalkyl, furyl, furylalkyl, pyrrolyl, thiazolyl, indolyl, indolylalkyl, quinoxalinyl or isoquinolinyl.

* * * * *

UNITED STATES PATENT AND TRADEMARK OFFICE
CERTIFICATE OF CORRECTION

PATENT NO. : 5,824,670
DATED : October 20, 1998
INVENTOR(S) : Stache et al.

It is certified that error appears in the above-identified patent and that said Letters Patent is hereby corrected as shown below:

Title page, item [57], replace in entirety with amended abstract below.

ABSTRACT

The invention relates to 17-deoxycorticoidsteroid-21-carboxylic esters of the formula I,

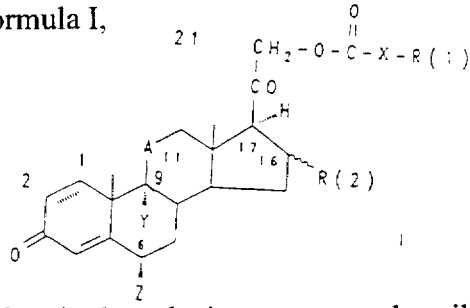

wherein the substituents are as described in the specification. The compounds formula I are obtained by reacting a compound of the formula II,

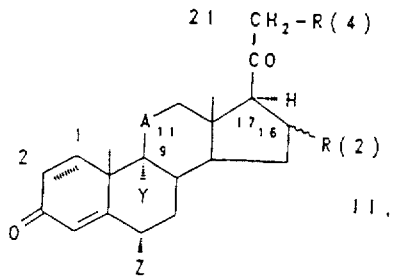

UNITED STATES PATENT AND TRADEMARK OFFICE
CERTIFICATE OF CORRECTION

PATENT NO. : 5,824,670
DATED : October 20, 1998
INVENTOR(S) : Stache et al.

It is certified that error appears in the above-identified patent and that said Letters Patent is hereby corrected as shown below:

in which R(4) is OH, Br, I, a sulfonic aryl ester group or a sulfonic alkyl ester group, with an activated carboxylic acid of the formula III, $$R(5)\text{-CO-X-R}(1) \qquad III.$$

The compounds of formula I possess very strong local and topical anti-inflammatory activity and exhibit a very good ratio of local to systematic and anti-inflammatory effect.

Signed and Sealed this

Eleventh Day of January, 2000

Attest:

Q. TODD DICKINSON

*Attesting Officer*    *Acting Commissioner of Patents and Trademarks*